(12) United States Patent
Ludwig

(10) Patent No.: US 6,960,321 B1
(45) Date of Patent: Nov. 1, 2005

(54) STERILIZATION OF FIRE SPRINKLER SYSTEMS

(76) Inventor: Jerome H. Ludwig, 12647 Crystal Lake Dr., Sun City West, AZ (US) 85375

( * ) Notice: Subject to any disclaimer, the term of this patent is extended or adjusted under 35 U.S.C. 154(b) by 650 days.

(21) Appl. No.: 09/410,916

(22) Filed: Oct. 1, 1999

(51) Int. Cl.$^7$ .............................. A61L 2/08; B08B 7/04; C02F 1/76; B05B 17/00; A62C 35/00

(52) U.S. Cl. ............................ 422/26; 422/28; 422/33; 422/34; 422/37; 422/109; 422/120; 134/18; 134/30; 134/37; 134/22.14; 210/754; 210/758; 210/764; 210/696; 210/701; 210/742; 137/186; 137/197; 137/238; 239/1; 239/266; 239/428.5; 169/17; 169/37; 169/38; 169/39; 169/40; 169/DIG. 29; 169/125; 138/1; 138/39; 138/764

(58) Field of Search ................................ 422/1, 26–27, 422/28, 33, 34, 37–38, 109, 120–122; 134/30, 134/37, 18, 22.14; 210/754, 758, 764, 760, 210/696, 701, 742; 137/197, 186, 238; 239/1, 239/428.5, 266; 169/DIG. 29, 125, 37–40, 169/17; 138/1, 39, 764; 15/104.03, 406

(56) References Cited

U.S. PATENT DOCUMENTS

| | | | | |
|---|---|---|---|---|
| 382,147 A | 5/1888 | Farrar | ...................... | 134/102.1 |
| 424,102 A | 3/1890 | Edds | ...................... | 134/102.1 |
| 1,355,074 A | 10/1920 | Cleveland | ...................... | 134/29 |
| 2,023,496 A | 12/1935 | Todd | .............................. | 87/5 |
| 2,065,462 A | 12/1936 | Olsson | ........................ | 141/1 |
| 2,324,804 A | 7/1943 | Gelderen | ...................... | 141/1 |
| 2,338,689 A | 1/1944 | Parker, et al. | .................. | 21/57 |
| 3,084,076 A * | 4/1963 | Loucks | ........................ | 134/22 |
| 3,493,323 A | 2/1970 | Demuth | ........................... | 21/2 |
| 3,762,874 A | 10/1973 | Berry | .............................. | 21/57 |
| 3,824,770 A | 7/1974 | Eckstein | ....................... | 55/279 |
| 3,893,832 A | 7/1975 | Perry, et al. | ................... | 55/268 |
| 3,984,302 A * | 10/1976 | Freedman et al. | ........... | 204/196 |
| 3,999,943 A | 12/1976 | Berry | ........................... | 21/108 |
| 4,301,113 A * | 11/1981 | Alguire et al. | ................... | 422/2 |
| 4,563,781 A | 1/1986 | James | ........................... | 4/542 |
| 5,051,193 A * | 9/1991 | Cummings, Jr. | ............. | 210/752 |
| 5,368,651 A * | 11/1994 | Esser | ......................... | 134/22.1 |
| 5,512,249 A * | 4/1996 | Singh | ......................... | 422/114 |
| 5,527,395 A | 6/1996 | Perry, et al. | .................... | 134/3 |
| 5,648,046 A | 7/1997 | Weibel | ......................... | 422/4 |
| 5,800,629 A | 9/1998 | Ludwig, et al. | ........... | 134/22.11 |
| 5,803,180 A * | 9/1998 | Talley | .......................... | 169/16 |
| 5,885,364 A * | 3/1999 | Hieatt et al. | | |
| 6,076,536 A * | 6/2000 | Ludwig et al. | ........... | 134/22.11 |
| 6,183,646 B1 * | 2/2001 | Williams et al. | ............. | 210/636 |
| 6,221,263 B1 * | 4/2001 | Pope et al. | .................. | 210/764 |

FOREIGN PATENT DOCUMENTS

| | | | | |
|---|---|---|---|---|
| FR | WO 95/00206 | * | 1/1995 | .......... A62C 37/50 |
| FR | 2 728 800 | * | 7/1996 | .......... A62C 35/58 |

OTHER PUBLICATIONS

English Abstract for French patent number 2 728 800.*
English Abstract for foreign patent number WO 95/00206.*

* cited by examiner

Primary Examiner—John Kim
Assistant Examiner—Monzer R. Chorbaji
(74) Attorney, Agent, or Firm—Wood, Herron & Evans, L.L.P.

(57) ABSTRACT

New and in-use fire sprinkler systems can be sterilized by employing antimicrobial gases. The gases include steam, oxygen, and chlorine. Water added to the system after sterilization can be sterilized to prevent the reoccurrence of microbiological contamination.

9 Claims, 1 Drawing Sheet

STERILIZATION OF FIRE SPRINKLER SYSTEMS

BACKGROUND OF THE INVENTION

In January 1997, the United States Environmental Protection Agency presented to the Congress of the United States of America their first report on the "Drinking Water Infrastructure Needs Survey" which defined an investment need of $138.4 billion over the next 20 years. $77.2 billion was determined for the replacement and rehabilitation of potable water transmission lines in order to deliver the quality and quantity of water required by customers. The problems found in the water distribution systems include (1) tuberculation which blocks the pipe and reduces the hydraulic capacity which then requires higher operating pressures and also reduces fire protection, (2) depletion of biocide due to the presence of tuberculation, organic matter and the microorganisms associated therewith, and (3) leaks resulting from microbiological and/or galvanic corrosion and higher operating pressures.

Fire protection systems are usually an extension of existing water distribution systems. The deterioration of piping, sprinkler heads and the hydraulics (the ability of the system to deliver water to design specifications) in fire protection systems is most frequently attributed to the quality of the water being supplied from the water distribution source, including potable water distribution sources. Contributing to the water quality feed problem is the fact that most fire protection systems are supplied through a "dead end" pipe connection from the water main to the fire protection system. These "dead ends" are notorious for containing all of the problem microbiological organisms that lead to the deterioration of the fire protection system. This is due to the stagnant nature of the water in the "dead end" which even allows biocides to be depleted and organisms to grow. Then, when the fire protection system is tested periodically, the stagnant, microbiologically contaminated water from the "dead end" is fed into the fire protection system which then begins or adds to the deterioration process.

In recent years, lawsuits have been filed against municipalities for supplying water that contains metal-hungry, corrosion-inducing bacteria which damage sprinkler systems and cause leaks that, in turn, further damage other assets. Municipalities argue that the water produced by their treatment plants meets or exceeds the specifications required for potable water. However, it is well documented that the quality of the water leaving the water treatment plant is not the same as that being consumed by the user after being transported through miles and miles of deteriorated distribution systems. This has recently led the EPA to require that potable water suppliers sample water at the user's taps and measure for lead and copper content ("The Lead and Copper Rule"). If the lead and/or copper content is over the maximum allowable content, then the supplier must take the appropriate action to lower the content to achieve acceptable levels. This is usually accomplished by the addition of passivation chemicals at the water treatment plant. Additional quality requirements by the EPA for water taken from the consumers tap are expected to be forthcoming in the future.

This situation is further compounded in fire sprinkler systems. For example, during periodic testing or under fire conditions, stagnant water which has been depleted of biocide and is now full of microbiological organisms from the "dead end" pipes contaminates the entire fire sprinkler system. In early 1996, the National Fire Protection Association (NFPA) began receiving reports regarding a significant increase in the number of problems involving the prevalence of pinhole leaks in fire sprinkler systems nationwide. A survey of the members was conducted in April of that year to determine the full extent of the problem. Pinhole leaks with dark brown or rust colored slime were reported on the interior of the piping. The source of this deterioration is now termed "Microbiologically-Influenced (or Induced) Corrosion" (MIC).

The NFPA's Pamphlet No. 13 "Installation of Fire Sprinkler Systems" is now revised to include and recognize MIC as a severe problem in fire protection systems and requires that it must be dealt with to ensure proper, long term fire protection system performance.

When it is determined that MIC is present and the eventual deterioration is underway, few options exist to deal with the problem in fire protection systems. Once pinhole leaks or nodules of tuberculation (which will markedly reduce water flow and which, under "fire" flow conditions, can break loose and block the sprinkler heads) are present, the affected pipe should be replaced. Then, steps must be taken to ensure microbiological infestation does not reoccur when the system is put back into service.

If there are no pinhole leaks or indications of tuberculation nodules, then thoroughly flushing the system with water containing biocides may reduce the problem. It is very difficult, however, to fully flush all of the pipe in a typical sprinkler system and ensure the removal of all microorganisms. Organisms can even penetrate the pipe threads at the fittings and may not be reached by a biocide flush. Also, if the system does not include a backflow prevention device on the supply line from a potable water main, only biocides which have been certified to NSF (National Science Foundation) International's Standard 60 may be employed to eliminate the contamination potential of a potable water feed system. Once the system has been flushed and placed in a restored but stagnant condition, microorganisms that have gone into a dormant state in the presence of the biocide can revive and thrive when the biocides are depleted.

If there are nodules of tuberculation present, but the integrity of pipe walls is still good, then pipe cleaning should be considered. U.S. Pat. No. 5,885,364 describes a chemical cleaning process which utilizes a chemical cleaning solution to remove the nodules of tuberculation that adhere to the interior walls of the pipe. Chemical cleaning, alone, can not guarantee sterilization of the system.

Mechanical cleaning technologies generally cannot be used in fire protection systems because of the elevations involved, the different sizes of small diameter pipe and the innumerable joints, elbows, etc. It would be more economical to replace the entire system.

Installation, replacement, repair, flushing or chemical cleaning of a fire protection system without sterilization and aseptic maintenance of the system merely postpones the inevitable re-infection and ultimate corrosion of the system. The need for a practical and efficient process to sterilize new and in-use fire protection systems, whether chemically cleaned or not, is urgent. Sterilized systems must also be maintained in an aseptic condition to ensure long term performance.

SUMMARY OF THE INVENTION

This invention is directed to a method of sterilizing a new or in-use fire sprinkler system employing an antimicrobial gas. A section of a fire sprinkler system contaminated with microorganisms is sterilized by isolating the section, delivering an amount of an antimicrobial gas for a duration and at a temperature sufficient to kill the undesirable microorganisms, and returning the now sterilized section to operation.

If the fire sprinkler system is in use, the water contaminated with microorganisms is preferably removed before delivery of the antimicrobial gas. Precautions are taken to prevent a sterilized section from being re-contaminated with extraneous microorganisms from the surrounding environment or the refill water. For example, to return an in-use section to normal operation, any remaining antimicrobial gas may be purged with a sterile gas and the sterile section charged with sterilized water. A second sterile gas, such as filtered air or ultraviolet irradiated air, may be used until the section is filled with sterilized water.

Sterilization can effectively be accomplished chemically or thermally. Antimicrobial gases suitable for chemical sterilization include ammonia, ozone, chlorine, bromine, oxygen, formaldehyde, sulfur dioxide, alcoholic vapors, nitrous oxide, sulfur trioxide, and ethylene oxide. For thermal sterilization by heat transfer, antimicrobial gases such as steam, nitrogen, air, inert gases and combustion gas can be delivered at temperatures sufficient to kill all microorganisms. It has been found that a steam temperature between about 100° C. to about 140° C. optimizes thermal sterilization.

Many fire sprinkler systems incorporate heat-sensitive sprinkler heads that must be inactivated before and during delivery of a heated antimicrobial gas. In one embodiment of the method, a gas temperature is selected that is below the activation temperature of the sprinkler heads, yet sufficient to kill the microorganisms. Alternatively, the heat-sensitive sprinkler heads may be removed and replaced with temporary fittings, such as a valve, a plug, or a condensate trap. Heated gas may be delivered through one or more of these temporary fittings. In addition, the temporary fittings can be used to direct gas flow to all points of the section in an amount, for a duration and at a temperature sufficient to kill the contaminating microorganisms. To monitor the sufficiency of the temperature, temperature sensors such as thermocouples and infrared thermometers may be located or directed at various positions in the section undergoing sterilization. Following sterilization, normal operation is reestablished by reinstalling the sprinkler heads which must also be sterilized.

Where heat losses during gas delivery limit the length of water distribution pipe that can be thermally sterilized, heated gas can be introduced at multiple locations in an isolated section. Alternatively, gas flow may be directed through a selected water distribution pipe to a specific outlet. Also, the temperature of the heated gas such as steam can be increased by adjusting the outlet gas pressure.

This invention provides a simple, low-cost and effective method for sterilizing fire sprinkler systems to prevent or inhibit microbiologically influenced corrosion, pinhole leaks, the deterioration of the hydraulics, and overall performance degradation.

Other advantages and objectives of this invention will be further understood with reference to the following detailed description and drawings.

DETAILED DESCRIPTION OF THE INVENTION

A. Microbiologically Influenced Corrosion

Microbiologically influenced corrosion (MIC) in fire protection systems is a very complex process. It is dependent on a multitude of factors including the type and quantity of microorganisms present; the water quality in terms of the amount of organic matter, sulfate ions, oxygen and other microorganism nutrients present; the pH; the biocide employed; the ambient temperatures; the type of metal involved in the system; and the maintenance program. All of these factors will vary from one location to another and should be considered when evaluating a problem involving MIC.

The principal type of microorganisms which will result in MIC are acid-producing bacteria, sulfate-reducing bacteria and iron bacteria. Aerobic bacteria and low nutrient bacteria also contribute to MIC by forming biofilms (slime) which promote the growth of the problem bacteria. Water samples and deposits from the sprinkler system can be tested for the presence of these bacteria with commercially available test kits or by sending the samples to a microbiological laboratory. Monitoring for MIC should include the microbiological analysis of both the source water and water from several locations in the system. Examination of the interior of the system, particularly near the water source, for evidence of microbiological growth, leaks, odor, slime or nodules should also be conducted.

Once the presence of microorganisms in the system has been detected, a more exhaustive study to determine the extent and severity of the MIC problem should be conducted, followed by the proper corrective action to ensure the long term viability of the fire protection system in case of a fire. Sprinkler system piping is generally of the thin wall variety due to the weight limitations imposed by hanging the system over head. Severe infestation resulting in diminished pipe wall thickness and/or leaks coupled with large nodules of tuberculation will usually require the replacement of some or all of the system piping. Upon completion of the renovation, the system should then be sterilized with an antimicrobial gas prior to being put back into service.

If the pipe wall has some pit degradation but is still structurally sound, the system is a candidate for chemical cleaning.

Likewise, if the nodules of tuberculation present would substantially reduce the water flow during a fire or could break loose to plug the sprinkler heads during a period of high flow, then the system should be chemically cleaned in order to restore the system to its design hydraulics. After chemical cleaning, the system should be sterilized with an anti-microbial gas prior to being put back into service.

If microbiological infestation is found to be in the early stages of development with little or no pitting of the pipe wall with only minor tuberculation present, then only antimicrobial gas sterilization should be performed.

Newly installed fire protection systems should be sterilized with antimicrobial gas prior to being commissioned. This is necessary because microbiological contamination of the components of the system will occur at any time prior to assembly, during storage, fabrication and assembly. Residual cutting oils are also food for microorganisms and they will rapidly infest all surfaces having the oil residues. If "dead end" water is used to fill a new system, the MIC process will begin immediately.

Traditional levels of oxidative biocides (such as chlorine, hypochlorites, chlorine dioxide, etc.) employed in water treatment to kill pathogenic organisms in potable water are not effective in killing all the MIC related bacteria at the level that the biocides are normally employed. Many bacteria, when exposed to a hostile environment, secrete a mucilaginous slime which encapsulates the bacteria and shields it from contact with the biocide. Then, when the biocide has dissipated, the bacteria again begin to grow. This is the process that occurs in the "dead ends" of water distribution systems which usually supply the water to the fire protection system.

Sulfate reducing bacteria are one of the prime causes of MIC in fire protection systems. They are anaerobic and are capable of converting sulfates to sulfides. This is the main cause of the hydrogen sulfide ("rotten egg") odor that occurs in most fire protection systems and is most noticed when the systems are tested by drawing water from various points along the system. The "rotten egg" odor coming from water samples is one of the first signs of microbiological activity in the system. Sulfate reducing bacteria cause serious localized corrosion of the system components.

Acid producing bacteria are also a prime MIC contributor. They are also anaerobic and generally are found with sulfate reducing bacteria. Organic acids are produced as a result of their metabolism.

These acids attack the iron in the fire protection system and cause the pit corrosion that leads to pinhole leaks. The iron is soiublized in the form of ferrous ion.

Another major contributor to MIC is iron bacteria. These bacteria convert soluble ferrous iron to insoluble ferric ion as part of their metabolic energy source. This results in deposits of iron oxide (rust) which builds up into nodules of tuberculation that result in diminished water flow in the pipe and which can be knocked off during water flow and plug the fire sprinkler heads. These organisms continue to thrive in combination with the acid producing (ferrous ion producing) and sulfate reducing bacteria in the nodules. The nodules continue to grow much like coral reef and significantly reduce the hydraulics of the system. When this occurs, the fire protection system must be chemically cleaned and then sterilized with an antimicrobial gas to restore the system. It must then be preserved with sterile water.

Aerobic, or slime forming bacteria, and low nutrient bacteria also contribute to MIC with their biofilms that harbor other bacteria and constitute part of the organic building blocks in the construction of the tubercles.

Microorganisms involved in corrosion are very small, i.e., starting at less than 0.2 $\mu$m. This allows them to easily penetrate down minute openings such as pipe threads, weld lines, metallic crystalline edges, etc., that are only several hundred micrometers in length. They can endure a wide range of ambient conditions, i.e., temperatures from 30 to 180° F., pH from 0 to 11, and oxygen concentrations from 0 to 100%. Many produce spores that resist even more severe environmental conditions and can survive in a dormant state for long periods of time before recolonizing on surfaces when the conditions are more favorable. They can resist many antimicrobial agents because of their ability to become impermeable to them by producing extracellular polysaccharides (slime layers) or by their ability to degrade them by excreting enzymes which can act outside the cells. They also can form communities of various microorganisms which interact synergistically to accomplish corrosive activity that would not occur individually. For these reasons and more, corrosive microorganisms (MIC) must be eliminated from fire protection systems to ensure the long term functionality they were designed to provide in case of an emergency.

B. The Antimicrobial Gasses and Preferred Mode

The inventive method involves sterilizing any new or old fire protection system that is microbiologically contaminated with organisms that have damaged or will ultimately deteriorate the integrity and performance of the system. The sterilization medium is an antimicrobial gas, preferably hot gases or steam. Other antimicrobial gases such as halogens, ozone, ethylene oxide, sulfur dioxide, sulfur trioxide, nitrous oxide, oxygen, alcoholic vapors, formaldehyde, and the like, can be used in the sterilization of those fire sprinkler systems where heat transfer sterilization is not practical.

In a preferred method, the antimicrobial gas is steam. In such a case, as much water as possible should be removed from the system by draining, blowing with air or sucking with vacuum. Then, the fire sprinkler heads should be removed since most sprinkler heads will activate at the sterilization temperatures employed. Depending on the position and orientation of the fittings, the sprinkler heads should be replaced with a plug valve or steam trap. Next, temperature sensors are employed in strategic locations to monitor that the entire system reaches the desired sterilization temperature. Finally, hot gas is introduced into the system through either the larger diameter pipes, i.e., main risers or headers, or through the sprinkler drops and risers or the ends of the lines, depending on the logistics of the system design. In some cases, particularly with large systems, it may be desirable to inject the hot gases at several points in order to achieve complete sterilization in a reasonable length of time.

When steam is employed, the valves are used to create a back pressure to allow the steam temperature to rise above the normal boiling point of water and to bleed off condensate. In some cases, the valves may be replaced with steam traps to accomplish the same task. In all cases the valves are used to direct the flow of hot gases to areas of the system being sterilized, but which have not yet reached the desired sterilization temperature.

The sterilization process setup will vary from sprinkler system to sprinkler system depending on its design and the location and orientation of the sprinkler heads, the headers, the risers, etc. Such logistics of sterilization can be easily determined from the teachings of this invention by one knowledgeable in the art. The processing conditions of treatment time, temperature and amount of sterilizing gas will vary depending upon the type of microorganisms, the amount of their buildup in the system, their sensitivity to the gas or temperature, properties of the gas at certain temperatures and similar factors. For sterilization with steam, we have found that at least about 120° C., for at least about 5 minutes, at a pressure of at least about 30 psi for the system under treatment, the processing conditions are satisfied.

When using steam as the hot sterilizing gas, the condensate may be allowed to drop to the floor or hoses may be attached to each valve or steam trap to collect the condensate into a container, manifold or reservoir. This will prevent water damage to whatever may be beneath the sprinkler section being cleaned.

When certain sprinkler systems above sensitive equipment, such as in computer rooms, high tech production areas and pharmaceutical production and packaging areas, cannot be sterilized practically with steam, a "non-condensable" hot gas such as air, nitrogen, combustion exhaust, etc., may be employed in these cases as the sterilizing gas. In cases when employing non-condensable gases, the valves will not be necessary to create a back pressure in order to achieve the desired temperature for sterilization of the entire system as when employing steam as the hot gas. Valves can be employed to direct the hot gas flow to all extremities of the system being sterilized.

When other active antimicrobial gases are employed such as chemically active ones, i.e., chlorine, ethylene oxide, etc., or hot gaseous vapor, i.e., alcohols, aldehydes, etc., the setup for the sterilization of the fire sprinkler system would be similar to that used with hot steam. The hoses connected to the valves are used to collect the antimicrobial gas for treatment, recovery or disposal of any undesirable effluent.

Once the fire protection system has been sterilized with hot gas (including steam), the hot sterilizing gas can be replaced by a supply of sterilized gas at ambient temperature, i.e., filtered air, compressed sterilized gases, etc. If a positive gas pressure is maintained on the sterilized system it will prevent microbiological contamination from the surrounding air.

The sprinkler heads and other plugs and fittings previously removed are then sterilized by dipping them in a biocide solution, i.e., alcohol, chlorine, etc., and reinstalled. Upon completion of the replacement with sterilized sprinkler heads, plugs and fittings, the system is sterile and is ready to be recharged with sterile water.

DETAILED DESCRIPTION OF FIGURES AND EXAMPLES

Figure 1:
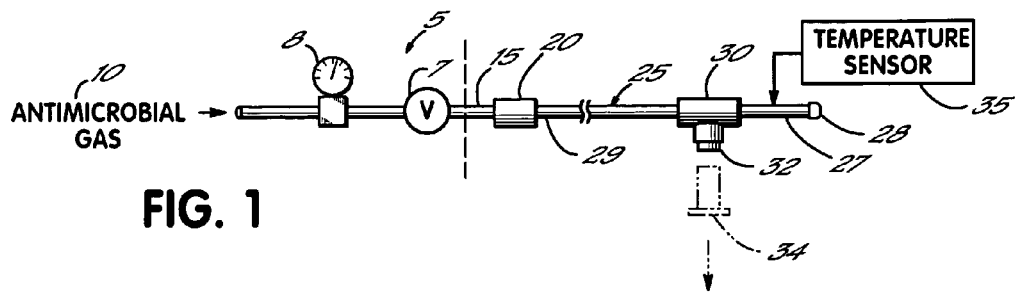
FIG. 1 is a schematic view of a system illustrating the method of this invention.

Referring to FIG. 1, a system is shown that uses an antimicrobial gas for sterilizing a section of a sprinkler system water distribution pipe contaminated with microorganisms. The test system includes a pressurized source 5 of an antimicrobial gas 10, a conduit 15 that has one end communicating with the source 5 to receive the pressurized antimicrobial gas 10, and an adapter 20 for coupling the opposing end of the conduit 15 to a pipe specimen 25. The conduit 15 includes a shut-off valve 7 for controlling the flow of the antimicrobial gas 10 and a pressure gauge 8 for indicating the pressure of the antimicrobial gas 10.

The pipe specimen 25 can originate from a section of a contaminated fire sprinkler system. Before sterilization, any microorganism-laden water that may fill the pipe specimen 25 is removed. To isolate the pipe specimen 25 for delivery of the antimicrobial gas 10, one end 27 is sealed with an end cap 28. The opposing end 29 of the pipe specimen 25 is mounted to one side of the adapter 20. When shut-off valve 7 of the pressurized source 5 is opened, the antimicrobial gas 10 will stream into the isolated pipe specimen 25 and, eventually, statically pressurize the pipe specimen 25 to the source pressure. The antimicrobial gas 10 is delivered for a duration, at a temperature, and in an amount sufficient to kill microorganisms and sterilize the pipe specimen 25. A vacuum assist may be used to evacuate air and to facilitate the addition of the antimicrobial gas.

According to the invention, microorganisms can be killed by chemical and/or thermal action. Antimicrobial gases suitable for killing microorganisms by chemical and/or thermal action include, but are not limited to, steam, ammonia, ozone, halogens, nitrous oxide, sulfur dioxide, sulfur trioxide, vaporized alcohols, vaporized aldehydes, vaporized formaldehyde, chlorine, bromine, oxygen, and ethylene oxide, and mixtures thereof.

A chemical used for sterilization that is liquid at ambient temperature must be heated above its boiling point to form a vapor suitable for delivery. For some antimicrobial gases, heated delivery may speed this chemical sterilization process.

A heated non-condensable antimicrobial gas, such as air, nitrogen, or combustion gas, is particularly useful when sterilizing a section of the fire sprinkler system over moisture-sensitive equipment, such as electronics.

Heated antimicrobial gases can be problematic if the pipe specimen 25 to be sterilized incorporates one or more temperature sensitive sprinkler heads 34 installed in system fittings 30. To avoid activating the sprinkler head, one approach is to deliver the antimicrobial gas 10 at a temperature below the activation temperature of the sprinkler head 34. However, certain gases 10 may be non-microbiocidal at a temperature less than the activation temperature for triggering the sprinkler head 34. Before using such gases at anti-microbiocidal temperatures, each sprinkler head 34 must be removed from the fitting 30 and replaced with a plug 32 or another temporary fitting such as, but not limited to, a valve or a condensate trap.

A temperature sensor 35, such as a thermocouple or an infrared-sensing device, can be used to measure the temperature at various positions along the length of the pipe specimen 25 during delivery of a heated antimicrobial gas 10. Since the end 27 is most distant from the source 5 of a heated antimicrobial gas 10, it will also likely be the coolest position due to heat losses in the intervening pipe length and the key location for monitoring the required temperature.

Figure 2:
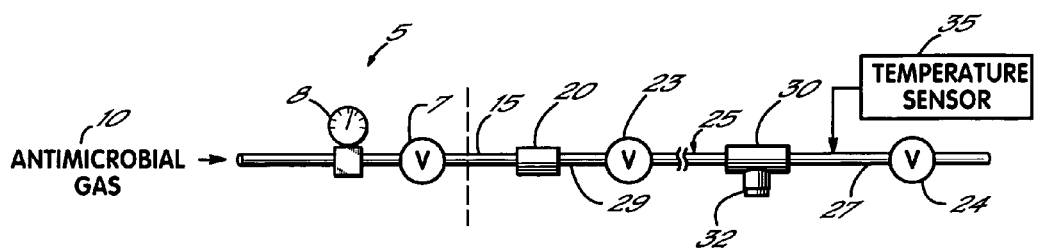
FIG. 2 is a schematic view of a system, similar to that of FIG. 1, illustrating the method of this invention when delivering a condensable antimicrobial gas.

Referring to FIG. 2, an alternative embodiment of the system is shown for use with a condensable antimicrobial gas, such as steam. In this specific embodiment, a valve 23,24 is added to each of the respective opposing ends 27,29 of the pipe specimen 25. The inlet ball valve 23 along with valve 7 can be opened and closed to control the flow rate of the antimicrobial gas 10 into the end 29 of the pipe specimen 25 from the pressurized source 5. Similarly, the outlet ball valve 24 can be adjusted to control the pressure and flow rate of antimicrobial gas 10 out of the opposing end 27 of the pipe specimen 25. By controlling the gas feed and exhaust, the pressure and therefore the temperature of the heated antimicrobial gas 10 can be controlled over the length of the pipe specimen 25 by adjusting the outlet ball valve 24. Using steam as the antimicrobial gas in a system similar to that shown in FIG. 2, it has been found that a temperature range between about 100° C. and 140° C. is optimum for killing the microorganisms responsible for the degradation of the water distribution pipes and water flow in fire sprinkler systems.

Figure 3:
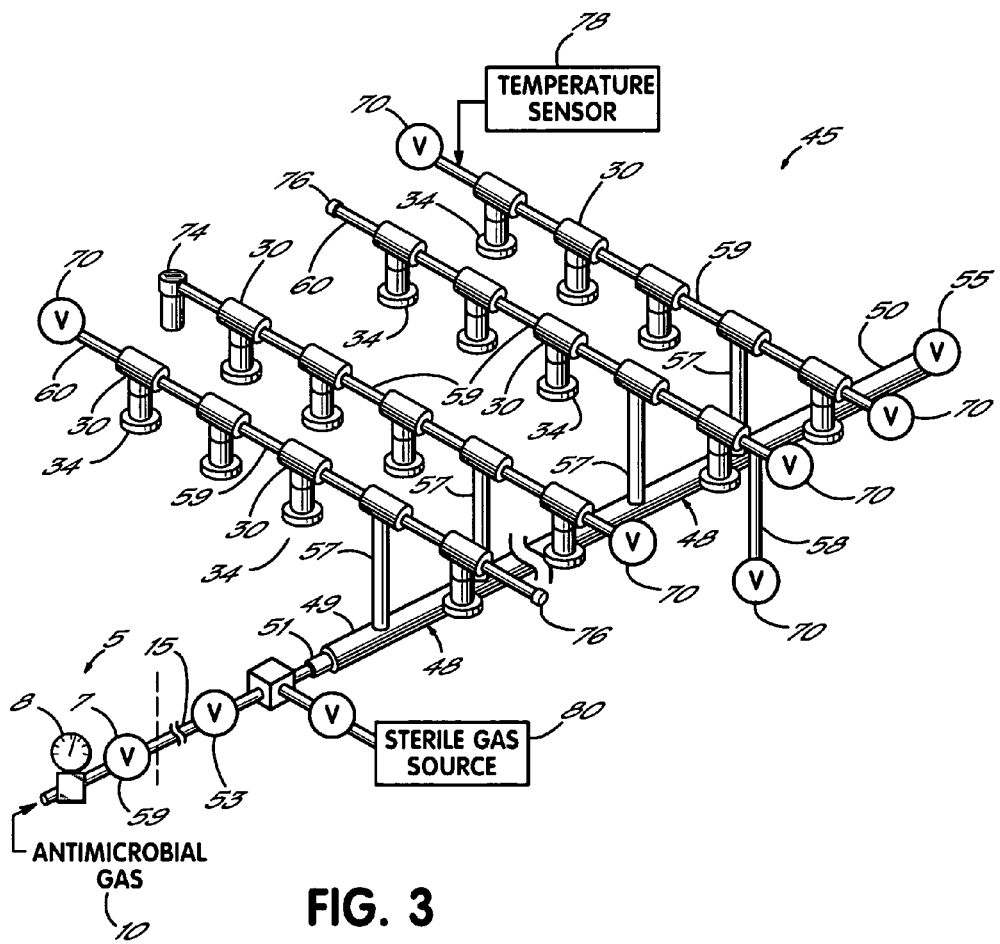
FIG. 3 is a diagrammatic illustration of a field system for sterilizing a section of water distribution pipe in a deployed fire sprinkler system.

FIG. 3 shows an installed section of a system for sterilizing a section of water distribution pipe in a fire sprinkler system. A section 45 of a fire sprinkler system generally comprises a large diameter header 48 that provides a source of pressurized water. Pipe 57 having an intermediate diameter branch vertically from the header 48 to feed water to a series of small diameter tributary pipes 59. The tributary pipes 59 are generally oriented transverse to the header 48. As a result, a number of tributary pipes 59 can be supplied by a single header 48. Fire sprinkler fittings 30 and heads 34 are stationed at periodic intervals along the length of each tributary pipe 59. A tributary pipe 59 can incorporate a vertical drop 58, if needed, for positioning a fire sprinkler head 34 in a specific location. The size of the section 45 that can be effectively sterilized depends upon the total length of pipe and the capacity of the source 5 for delivering pressurized antimicrobial gas. Expansive fire sprinkler systems may necessarily have to be sterilized by sections.

To practice the method of this invention, the section 45 of the fire sprinkler system is isolated for delivery of the antimicrobial gas 10. In the embodiment shown in FIG. 3, one end 49 of a header 48 is disconnected from its feed line (not shown). As with the preceding test systems, an adapter 51 and an inlet ball valve 53 are applied to connect the end 49 of the header 48 to the conduit 15 communicating with the source 5 of the antimicrobial gas 10. The opposing end 50 of the header 48 is disconnected to receive an outlet ball valve 55. It should be understood that the conduit 15 can be of any practicable length. For example, the source 5 of antimicrobial gas 10 can be located outside of the building housing the fire sprinkler system.

A tributary pipe 59 may be disconnected at certain strategic locations, such as the pipe flanges or ends 60. For example, a ball valve 70 can be attached so that an additional source 5 of pressurized antimicrobial gas 10 can be attached. In an embodiment of the method of the present invention that delivers a condensable antimicrobial gas, such as steam, a ball valve 70 attached at the end 60 of a tributary pipe 59 may serve other functions, such as draining condensate or preferentially directing the flow of antimicrobial gas 10. Alternatively, other types of temporary fittings may be attached to an end 60, such as a cap 76 or a condensate trap 74.

Before delivering the antimicrobial gas 10, any contaminated water held by the isolated section 45 is flushed to the extent practicable by, for example, suctioning, draining, or pressurizing with compressed air. Alternatively, the flow of antimicrobial gas 10 itself could be used to flush a substantial amount of the contaminated water from the isolated section 45. Of course, flushing is unnecessary if the fire sprinkler system is new and has not yet been put into service.

The inlet ball valve 53 is opened to permit pressurized flow of antimicrobial gas 10 from the source 5 into the isolated section 45. If no other valves 55,70 are open, the antimicrobial gas 10 will diffuse into the pipes of the section 45. The antimicrobial gas 10 is delivered for a duration, at a temperature, and in an amount to kill any undesired microorganisms. In some circumstances, it may be desirable to open the outlet ball valve 55 or a ball valve 70 on a tributary pipe 59 to purge the air from the section 45 as the antimicrobial gas 10 is delivered to avoid diluting its strength.

Following sterilization, before returning the fire sprinkler system to operation, the sterility of the freshly sterilized section 45 should be maintained. One way to do so is to introduce and maintain a pressurized flow of a second sterile gas 80, such as filtered air or ultraviolet irradiated air. The positive pressure of sterile gas 80 will flow out of any momentary breaks as valves and any temporary fittings are removed. As a result, external microorganisms cannot enter the sterilized section. The sterilized section is returned to normal operation by reversing the isolation procedure. The inlet and outlet valves 53,55 are removed and any other temporary fittings such as ball valves 70, condensate traps 74 and caps 76 are removed. If desired, the antimicrobial gas 10 can be purged from the sterilized section.

After the section is returned to normal operation, it is preferable to charge the sterilized section with a sterilized water. Recharging the section with microorganism-laden water will result in recontamination and eventual reinitiate MIC as the microorganisms repopulate the section.

If the antimicrobial gas 10 is heated, certain precautions must be taken. Operational fire sprinkler systems typically incorporate at least one heat-sensitive sprinkler head 34 that will be activated if the environment of the sprinkler head exceeds a threshold temperature. As mentioned above, one approach is to deliver the antimicrobial gas 10 at a temperature below the activation temperature of the sprinkler heads 34. However, the temperature for effective sterilization using a specific antimicrobial gas may exceed the activation temperature needed to trigger the sprinkler head 34. In that instance, each sprinkler head 34 must be removed and replaced with a temporary fitting such as, but not limited to, a ball valve 70, a plug 72, or a condensate trap 74, before the heated antimicrobial gas 10 is delivered. After the section 45 is sterilized, each temporary fitting is removed. Before reattachment to their normal locations on the water distribution pipes 59 of the section, it is preferable to sterilize the detached sprinkler heads 34, for example, by dipping them into a biocide.

During the delivery phase of the present method, ball valves 70 that have replaced fire sprinkler heads 34 can be used as additional entrances for the delivery of the antimicrobial gas 10. In large systems, these additional points of entry may be needed to introduce the antimicrobial gas for a duration, at a temperature, and in an amount sufficient to kill microorganisms.

If a condensable heated antimicrobial gas such as steam is delivered, the ball valves 70 are used to direct the flow of antimicrobial gas 10 so that all water distribution pipes in the section 45 will reach a temperature sufficient for thermal sterilization. Alternatively, condensate traps 74 can be used to remove the condensate from a condensable antimicrobial gas 10 and elevate its temperature.

For heated antimicrobial gases 10, one or more temperature sensors 78 can be used to measure the temperature of the water distribution pipes at various positions in the section 45 during gas delivery. Appropriate temperature sensors 78 include, but are not limited to, thermocouples and infrared-sensing devices. For effective thermal sterilization, of particular concern is whether the extremities of the section most distant from the source of pressurized heated gas reach a temperature sufficient to kill microorganisms therein.

The following examples further illustrate the antimicrobial gas sterilization process, particularly with pressurized steam.

Example 1

A 1-inch diameter microbiologically contaminated fire sprinkler pipe having one sprinkler head was obtained from a known contaminated system. The end of the pipe was capped, the sprinkler head was removed and plugged, the pipe was then filled with microbiologically contaminated source water and the other end capped.

A stream sterilization test of the pipe was conducted as shown in FIG. 1. One end cap of the pipe was removed and the contaminated water poured out of the pipe and a pre-sterilization sample of the water and scrapings from the interior pipe wall were taken under sterile conditions for microbiological testing employing a MICkit™ supplied by Bioindustrial Technologies, Inc., Georgetown, Tex. The microbiological samples were incubated for three weeks at 35° C. and observed for microbiological growth.

After pre-sterilization sampling, the pipe was connected to an adapter attached to the steam source (a 10-horsepower, 400,000 BTU Boiler) having a shut-off ball valve and a pressure gauge. A thermocouple was attached to the end cap to determine the exterior surface temperature of the end of the test pipe sample.

Steam was then injected into the test pipe by opening the ball valve slowly with the steam pressure at 30 lbs pressure (135° C.). The temperature at the end of the test pipe rapidly rose to 94° C. and then appeared to remain nearly constant. The ball valve was then closed and the pipe cooled to room temperature. The condensate water and scrapings from the interior of the test pipe were collected by removal of the pipe from the adapter under sterile conditions. The samples so collected were microbiologically tested as above.

The end cap was then replaced with a ball valve and the steam sterilization was repeated. The ball valve at the end of the pipe was opened slightly to allow condensate and live steam to escape. The temperature at the end of the pipe rapidly rose to 110° C. The test was terminated by closing the ball valves and allowing the pipe to cool to room temperature. The pipe was again sampled for microbiological testing as above.

The results of the microbiological testing are as follows (organisms per milliliter):

| Sample | LNB | IRB | APB | SRB |
| --- | --- | --- | --- | --- |
| Pre-steam | 100–1000 | <1 | <1 | 100–1000 |
| 94° C. | Negative | Negative | Negative | Negative |
| 110° C. | Negative | Negative | Negative | Negative |

NOTE:
LNB = Low Nutrient Bacteria
IRB = Iron Related Bacteria
APB = Acid Producing Bacteria
SRB = Sulfate Reducing Bacteria It can be concluded from these results that the fire sprinkler pipe was sterilized of bacteria by employing regulated steam flow at both 94° C. and 110° C.

However, to insure that spores (i.e., sulfate reducing bacteria) are also killed, temperatures of 121° C. are necessary. In order to achieve that temperature, the steam sterilization must employ pressurized steam flow (steam pressures of about 30 psi) through the pipe under controlled conditions.

Example 2

The steam sterilization pipe test was further modified for the following examples, as shown in FIG. 2, in order to achieve the higher sterilization temperatures. Two ball valves were attached to each end of the fire sprinkler pipe being tested in order to control the inlet steam pressure and flow, the outlet steam pressure flow, and to drain condensate from the test pipe.

Microbiologically contaminated water was obtained from a "dead end" water feed-line to a fire protection system and was assayed microbiologically using the MICkit™ giving the following results after only 2 days of incubation at 35° C.:

| LNB | IRB | APB | SRB | APC* |
| --- | --- | --- | --- | --- |
| Positive | Negative | Positive | Positive | >1000 |

*APC = Aerobic plate count of the number of colony forming units per mil. of water No further change in the results were noted after 15 days of incubation.

A new 1-inch diameter pipe section with fittings, as shown in FIG. 2, was filled with the microbiologically contaminated water and stored at ambient temperatures for 16 hours. The water was removed and was re-analyzed microbiologically. The same result showing residual microbiological contamination was reached after only 5 hours of incubation.

The infected pipe was then steam sterilized as shown in FIG. 2. The steam was allowed to slowly enter the pipe by regulating the input ball valve with the outlet ball valve open. Steam flowed through the pipe, heating it rapidly to near 100° C. The outlet ball valve was then nearly closed allowing the steam pressure in the pipe to increase. The temperature at the end of the pipe reached 135° C. and was kept there for five minutes. The inlet and outlet ball valves were closed and the pipe with the valves closed was removed and cooled in a stream of water. A small amount of sterile water (autoclaved at 121° C. for 15 minutes) was added to the sterilized pipe and the pipe raised, lowered and rotated to rinse the inside of the pipe system. The pipe was then opened and the water and scrapings from the side of the pipe were taken using sterile techniques for microbiological analysis.

The microbiological results on this sample were all negative for LNB, IRB, APB, SRB and were <1 for APC after incubation for 15 days.

This demonstrates that fire protection systems when contaminated with "dead end" (microbiologically contaminated) water, can be sterilized with hot gas (steam) treatment.

Example 3

The sterilized pipe from Example 2 was then filled with potable tap water containing 50 ppm sodium hypochlorite and allowed to stand at ambient temperature. The sodium hypochlorite, being an oxidizing agent, rapidly dissipated when in contact with the interior iron pipe surface. Analysis of the water after 24 hours showed 0 ppm sodium hypochlorite.

The water was left in the sterilized pipe for an additional seven days and was then sampled and assayed for microorganisms. The microbiological results were all negative for LNB, IRB, APB, SRB and <1 for APC.

This demonstrates that a sterilized fire protection system when filled with sterile water will remain sterile. Other biocides or methods of sterilization of the feed water, i.e., ultraviolet radiation, distillation, micro filtration, etc., may be used to prepare the sterile water to charge the sterile fire sprinkler system.

Example 4

A piece of pipe was removed from a fire protection system that had been chemically cleaned and filled with non-sterilized source water, capped and delivered to the laboratory for sterilization and testing. A sample of the water and scrapings from the inside of the pipe were taken for microbiological analysis. The microbiological test results were: LNB—positive; IRB—negative; APB—positive; SRB—negative; and APC —>1000, after 2 days incubation with no change after 15 days.

The drained pipe was then sterilized as in Example 2 (per FIG. 2) using steam and a temperature of 135° C. by controlling the inlet and outlet ball valves. The ball valves at the ends of the pipe were then closed, the pipe removed from the test station and cooled with water. A small amount of sterile water was introduced and the inside of the pipe rinsed with it for several minutes. The pipe was then opened and the water and scrapings from the side of the pipe taken for microbiological analysis.

The microbiological results were: LNB—negative; IRB—negative; APB—negative; SRB—negative; and APC—<1, after 15 days.

This demonstrates that chemically cleaned fire protection systems which are still microbiologically contaminated, can be sterilized by the process of this invention.

Example 5

Microbiologically contaminated water obtained from a "dead end" water feed line to a fire protection system employed in Example 2 was placed in the sterilized pipe from Experiment 4 and the pipe sealed by closing the two ball valves. The original "dead end" water had a microbiological assay of:

LNB and APB—positive; IRB and SRB—negative; APC —>1000

After 16 hours this water was drained from the pipe section and replaced with potable tap water sterilized with 50 ppm of sodium hypochlorite. After standing overnight at ambient temperature, the biocide had dissipated as expected. The water was then sampled and the following results were obtained after incubation for 15 days:

LNB—positive; IRB, APB and SRB—negative; APC —<1

This example demonstrates that microbiological contamination of sterilized pipe cannot be made sterile again by the use of oxidizing biocides. Care should be taken that all water entering the fire protection system after hot gas sterilization must be sterile in order to keep the system sterile and functional over the long term.

Example 6

Using a large section of a fire sprinkler system, similar to that shown in FIG. 3, having a 50-foot, 4-inch diameter header with 5, 1¼-inch diameter tributary pipes each having five sprinkler heads in the vertical position and one having a drop with a sprinkler head, one end of each tributary line was isolated from the sprinkler system by opening the respective flanges and attaching a ball valve. Sprinkler heads at the opposing ends of the respective tributary pipes and at a drop were also replaced with ball valves. A drain valve was installed at the low end of the header pipe to allow drainage of condensate at that point. In this case, flexible hose was attached to the ball valves at the end of the sprinkler lines and the drain valve in order to collect any condensate in drums rather than allowing it to drop randomly to the floor. A steam inlet valve, pressure gauge and thermocouple were attached to the inlet of the header pipe. Thermocouples were also attached at the opposing end of the header and at the furthest distance from the steam injection point. The remaining sprinkler heads were removed and replaced with plugs.

A 10-horsepower (335,000 BTU) gas fired boiler was used to generate the steam for the sterilization of the system. The boiler was placed outside of the building and a hose of an estimated 80 feet in length was used to transfer the steam from the boiler to the inlet of the header 30 feet above the floor.

As a general rule, the minimum boiler size can be calculated as one BTU per pound of pipe heated per degree Fahrenheit increase in temperature. In this case, the pipe was calculated to weigh about 1363 lbs (including a 25% safety factor), and the desired temperature increase was from ambient of 80° F. to 250° F. (or, 121° C. in order to kill spores and all bacteria). Thus, the minimum boiler size would be:

Boiler size=1 BTU per lb per °F.×1863 lbs×(250−80° F.)= 318,000 BTU

Such a boiler was employed and, with the expected heat loss from the 80-foot steam feed line, was considered marginally acceptable.

The system was previously tested and assayed microbiologically. The results were:

LNB—positive; IRB, APB and SR—negative

Steam was applied to the isolated system. Temperatures at the monitored locations were slowly increased to the 90° C. range. Condensate was drained from the drain valve without the temperature increasing substantially at the other locations. All ball valves were closed, except for the one at the most distant location from the inlet, to allow the steam to flow to that position. Within 10 minutes the temperature at the most distant position reached 123° C., two degrees more than that required to kill all spores.

This example demonstrates that, even with an undersized boiler, the desired maximum temperature for sterilization can be achieved at the furthest point in the system being sterilized. Once that point has been sterilized, the ball valve at that location is closed and another location's ball valve is opened until the desired temperature is achieved, and so forth. Naturally, a larger boiler or a combination of smaller boilers can achieve the desired sterilization temperatures in a shorter period of time.

The use of steam traps in place of ball valves would reduce the manpower required to get the condensate out of the system in order to achieve the desired temperature throughout the system in the shortest period of time.

In view of the above detailed description, other process variations to sterilize fire protection systems by the antimicrobial gas sterilization process disclosed in this invention will be apparent to a person of ordinary skill in the art without departing from the scope of this invention.

What is claimed is:

1. A method for steam sterilizing a fire sprinkler system comprising
    isolating a section of a water distribution pipe in a fire sprinkler system for the delivery of steam, wherein said water distribution pipe includes a plurality of heat-sensitive sprinkler heads and contains water,
    removing the water from said section of the system,
    utilizing a temperature sensor to detect the temperature at a position in said section of the system,
    inactivating the sprinkler heads during the delivery of the steam by removing said sprinkler heads and replacing them with temporary fittings,
    delivering said steam into said section for a duration at a temperature and in an amount sufficient to kill microorganisms and sterilize the section, and
    returning said sterilized section in the system to operation.

2. The method of claim 1 further comprising the step of purging said steam from said sterilized section with sterile gas.

3. The method of claim 2 wherein a second sterile gas is introduced under pressure into the pipe section to maintain sterility.

4. The method of claim 3 wherein said second sterile gas is selected from the group consisting of filtered air and ultraviolet irradiated air.

5. The method according to claim 1 or 2 further comprising charging said sterilized section in the system with sterilized water.

6. The method of claim 1 comprising maintaining the sterility of the section upon returning to operation.

7. The method of claim 1 wherein said temporary fitting is a valve, a plug, or a condensate trap, or combinations thereof.

8. The method of claim 1 wherein the temperature of said steam is between about 100° C. to about 140° C.

9. The method of claim 1 wherein said temporary fittings are replaced with sterilized sprinkler heads for operation of said system.

* * * * *